United States Patent [19]

Dwiggins et al.

[11] Patent Number: 4,618,579

[45] Date of Patent: Oct. 21, 1986

[54] RAW STARCH SACCHARIFICATION

[75] Inventors: Bruce L. Dwiggins; Carl E. Pickens, both of Decatur; Carl W. Niekamp, Forsyth, all of Ill.

[73] Assignee: Genencor, Inc., South San Francisco, Calif.

[21] Appl. No.: 656,051

[22] Filed: Sep. 28, 1984

[51] Int. Cl.$^4$ .................. C12P 19/20; C12P 19/14; C12N 9/34; C12R 1/645

[52] U.S. Cl. ........................ 435/96; 435/99; 435/205; 435/911

[58] Field of Search ................ 435/96, 99, 205

[56] References Cited

U.S. PATENT DOCUMENTS

| | | | |
|---|---|---|---|
| 2,853,451 | 1/1952 | Wallerstein et al. | 195/11 |
| 3,783,100 | 1/1974 | Larson et al. | 195/31 |
| 3,912,590 | 10/1975 | Slott et al. | 195/31 |
| 3,922,196 | 11/1975 | Leach et al. | 435/99 X |
| 3,922,197 | 11/1975 | Leach et al. | 435/99 X |
| 3,922,198 | 11/1975 | Kuske et al. | 435/99 X |
| 3,922,199 | 11/1975 | Hebeda et al. | 435/99 |
| 3,922,200 | 11/1975 | Walon et al. | 435/96 X |
| 3,922,201 | 11/1975 | Hebeda et al. | 195/31 |
| 4,009,074 | 2/1977 | Walon | 195/31 |
| 4,017,363 | 4/1977 | McMullen et al. | 195/31 |
| 4,092,434 | 5/1978 | Yoshizami et al. | 426/13 |
| 4,113,509 | 9/1978 | Leach et al. | 127/29 |

OTHER PUBLICATIONS

Evers et al, Die Starke vol. 23, pp. 16–18 (1971).
Walker et al, Biochemical Journal vol. 86, pp. 452–462 (1963).
Jones, Cereal Chemistry vol. 17, pp. 133–169 (1940).
Sandstedt et al, Journal of Japanese, Society of Starch Science, vol. 17, No. 1 pp. 215–228 (1969).
Abstract of Japanese Patent Publication No. 59-140,896 published Aug. 13, 1984.
Taylor et al, Carbohydrate Research vol. 61, pp. 301–308 (1978).

*Primary Examiner*—Lionel M. Shapiro
*Attorney, Agent, or Firm*—James G. Passé

[57] ABSTRACT

A multi-step process is provided for solubilizing and saccharifying granular starch slurries of between 20 and 60% d.s. starch. In a first step, an enzyme mixture exhibiting raw starch hydrolyzing activity is added to the slurry and maintained in contact therewith until at least a substantial portion but less than all of the starch is solubilized. The resulting syrup is separated from the remaining insoluble fraction. In a second step, the insoluble fraction is used to prepare a second slurry containing less than about 20% d.s. starch, and this second slurry is solubilized with a raw starch hydrolyzing enzyme preparation until substantially all (e.g., at least about 95% or more) of the starch is solubilized. The pooled syrup from the two steps is over about 20 weight percent saccharides, at least about 95% of which is glucose.

24 Claims, No Drawings

RAW STARCH SACCHARIFICATION

FIELD OF THE INVENTION

The present invention is directed to the conversion of starch to glucose, and more particularly to direct enzymatic conversion of a high solids granular starch slurry directly to glucose.

BACKGROUND OF THE INVENTION

A large number of processes have been described for converting starch to a monosaccharide, glucose. Glucose has value in itself, and also as a precursor for other saccharides such as fructose. Glucose may also be fermented to ethanol or other fermentation products.

The ability of alpha-amylase to hydrolyze raw (unpasted) starch and produce water soluble oligosaccharides has been known since the early 1900's, Reichert, E. T., *Publication of the Carnegie Institution at Washington*, No. 173, Part 1 (1913). Subsequently, other enzymes have been found that hydrolyze unpasted starch, most notably glucoamylase, which converts granular starch directly to glucose, Evers, A. D. et al., *Die Starke* 23 (1971), p. 16. The ability of an enzyme to hydrolyze granular starch is associated with the enzyme's ability to be adsorbed on the starch, Walker, G. J. et al., *Biochemical Journal* 86 (1963), p. 452. The extent of hydrolysis is related to the specific type of starch (corn, potato, wheat, etc.); and its physical condition (granule size; granules intact, fractured, swollen, abraded, etc.), the specific enzyme type and source; the starch and enzyme concentration; the temperature; the pH; and other factors, (Jones, C. R., *Cereal Chemistry*, 17 (1940), p. 133; Sandstedt, R. M. et al., *Journal of the Japanese Society of Starch Science*, Vol. 17 (1965), p. 215). The particular effects of these variables are generally only empirically understood.

Several processes for the commercial, low temperature, enzymatic solubilization of granular starch have been proposed, U.S. Pat. Nos. 2,583,451 issued Jan. 22, 1952 to Wallerstein et al; 3,922,196 issued Nov. 25, 1975 to Leach et al; 3,922,197 issued Nov. 25, 1975 to Leach et al; 3,922,198 issued Nov. 25, 1975 to Kuske et al; 3,922,199 issued November 1975 to Hebeda et al; 3,922,200 issued Nov. 25, 1975 to Walon et al and 3,922,201 issued Nov. 25, 1975 to Hebeda et al. Generally, an alpha-amylase is used at pH 4 to 6 at 40° C. to 75° C. to produce a low D. E. syrup. Simultaneously or subsequently, a saccharifying enzyme, such as fungal alpha-amylase, beta-amylase, or glucoamylase may be used at a suitable pH and temperature to produce the desired hydrolysis. The major advantage of such procedures are that they eliminate the high temperature cooking step at 100° C. to 150° C. in presently used syrup processes (U.S. Pat. No. 3,783,100 issued Jan. 1, 1974 to R. F. Larson et al and U.S. Pat. No. 3,875,140 issued Apr. 1, 1975 to Barker et al). Important disadvantages are increased enzyme costs, incomplete solubilization of starch resulting in the need for subsequent starch recycle, mud (fiber, protein and fat) separation problems, and microbial contamination problems.

Recently, it has been discovered that certain fungi, particularly species of the genus Humicola secrete a mixture of enzymes, including enzymes with glucoamylase activity, which efficiently hydrolyze raw (unpasted) starch granules. The ability to hydrolyze starch in granular form is referred to herein as raw starch hydrolyzing (RSH) activity. Enzyme preparations having, in either crude or more refined forms, RSH activity will be referred to herein as RSH enzyme preparations.

RSH preparation obtained from species of the genus Humicola, particularly the species *Humicola grisea* var. *thermoidea*, which is hereinafter referred to as Humicola RSH enzyme preparation, has the following characteristics. The Humicola RSH enzyme preparation hydrolyzes raw or granular starch, including straight- and branch-chained starches, and hydrolyzes the starch substantially entirely to glucose. This enzyme preparation is characterized by including a glucoamylase enzyme (EC 3.2.1.3) having an isoelectric point higher than pH 8.0 and a proteinaceous material having glucoamylase-potentiating activity which, in cooperation with the glucoamylase, catalyzes the hyrolysis of the granular starch. Said enzyme preparation is further characterized in that the glucoamylase fraction adsorbs on carboxymethyl cellulose, whereas a fraction containing material exhibiting potentiating activity, or "potentiating factor", is not adsorbed by carboxymethyl cellulose. The Humicola RSH preparation has the ability, for example, to hydrolyze granular starch in a 15% starch solids suspension in water to a solution of saccharides of at least 97% by weight glucose, dry substance basis (d.s.b.), with essentially no starch residue in the absence of debranching enzyme or added alpha-amylase when the hydrolysis is carried out at a pH of between about 5.0 and 7.0, the optimum pH range, and at a temperature of 55° C.

Although certain RSH enzyme preparations will substantially completely hydrolyze granular starch slurries at about 15 weight percent starch, dry solids (d.s.) to produce a high percentage glucose syrup, they generally do not completely solubilize starch in slurries of higher concentration within a reasonable time or provide sufficiently high percentages of glucose.

The ability to hydrolyze and saccharify starch that is raw or only partially pasted represents an important energy savings. Pasting is generally carried out at temperatures of 100° C. to 130° C. and upwards, therefore requiring significant input of thermal energy. RSH enzyme preparations, on the other hand, catalyze starch saccharification efficiently at relatively low temperatures (e.g., at 65° C. or less) and there is no need to heat the starch at any time to higher temperatures. However, starch slurries that are to be hydrolyzed with RSH enzyme preparations may be initially swelled at somewhat higher temperatures (e.g., 65° C. to 100° C.) to hasten the hydrolyzing process. Such a swelling procedure may be considered a partial solubilization and pasting step; nevertheless, starch subjected to these temperatures for short periods of time remains substantially in granular form.

It would be desirable for several reasons to use RSH enzyme preparations to solubilize and saccharify starch slurried at higher solids levels (e.g., between 20 and 60 weight percent starch, and more particularly between about 25 and about 40 weight percent starch, d.s.) than the 15% d.s. level that may generally be hydrolyzed by certain RSH enzyme preparations in a one-step reaction. Higher starch content slurries require less processing reactor tank space. The resulting saccharide solution or syrup is more highly concentrated, and thus, less energy is required for removing water therefrom to further concentrate or dry the same. When slurries higher than 15% solids are hydrolyzed with RSH enzyme preparations, a more concentrated saccharide solution is typically produced; however, in a reaction conducted for a reasonable period of time, a substantial amount of the starch remains insoluble, and unless this remaining starch can also be solubilized or otherwise used, the unsolubilized starch represents a substantial economic loss.

When high starch concentration slurries are enzymatically hydrolyzed with RSH enzyme preparations, hydrolysis generally proceeds at an appreciable rate only for a certain time period, typically about 48 hours. After this, the rate of hydroysis drops off considerably. With glucose being produced at lower rates, it is an inefficient utilization of reactor tank space to allow the reaction to continue. Perhaps more importantly, however, with high glucose concentrations, a significant amount of undesired disaccharide formation occurs and such disaccharides are difficult to hydrolyze. Thus the percent of glucose in the syrup decreases and the percent of higher saccharides increases. Such products are undesirable. For example, if glucose syrup is converted to a high fructose syrup, the higher saccharides do not contribute to the sweetness and may even detract from the sweetness. For these reasons, high solids starch slurries cannot generally be satisfactorily hydrolyzed by RSH enzyme preparations in a single step.

Raw starch, such as raw corn starch, contains in addition to the starch, fiber, protein and fat, which comprise an insoluble sludge or "mud" upon partial solubilization and saccharification of the starch. As the mud builds up in the process system, efficiency of enzymatic starch hydrolysis diminishes. As such, it is not feasible to produce highly concentrated syrups by a simple process of continuously adding additional starch slurry to a reaction vessel as syrup is continuously or periodically removed therefrom. Accordingly, the present invention seeks to solubilize and saccharify high solids granular starch slurries and to recover in solubilized and saccharified form as much starch as possible from the insoluble mud.

It is a primary object of the present invention to provide an economical process which converts a slurry of high solids granular starch substantially completely to glucose (dextrose) at a low temperature. It is a further object of the present invention to provide such a process which facilitates removal of insoluble "mud" (fiber, protein and fat) from the predominantly glucose syrup which is produced.

SUMMARY OF THE INVENTION

An aqueous slurry of milled granular starch of between about 20 and 60 weight percent starch, dry substance (d.s.), is converted in a multi-step process substantially entirely to a syrup containing a high percentage of glucose using raw starch hydrolyzing (RSH) enzyme preparations. In a first step, the enzyme preparation is added to a first starch slurry and allowed to act for a period of time sufficient to solubilize and saccharify at least a substantial portion (e.g., at least about 25, preferably at least about 50 and most preferably at least about 60 percent), but less than all, of the starch contained in said first starch slurry. The reaction is preferably terminated before the percent glucose in the solubilized saccharide product, d.s., drops to about 95 percent, and this will usually occur when the conversion of starch is below about 95 percent. The solubilized saccharide product or syrup of the first step, which generally will contain at least 22% d.s. saccharides, is separated from insolubles which yet contains substantial amounts of unsolubilized starch. The insolubles are reslurried to form a second slurry having a starch concentration of less than 20 percent by weight d.s. The starch in said second slurry is then hydrolyzed by contacting same with an RSH enzyme preparation for a time sufficient to solubilize and saccharify substantially all of the starch contained in said second slurry. The remaining insolubles, containing fiber, protein and fat, are removed by centrifugation, filtration or other suitable separation means, from the syrup prepared in the second step. The syrup from the second step of the process can be pooled, if desired, with that from the first step and, in that event, the resulting pooled syrup will generally contain upwards of 20 percent by weight saccharides, at least 95% of which is glucose.

DETAILED DESCRIPTION OF THE PREFERRED EMBODIMENTS

In accordance with the present invention, slurries of 20 to 60 (preferably from about 25 to about 40) weight percent granular starch are substantially completely solubilized and saccharified with an RSH enzyme preparation in a multi-step process to produce a pooled syrup with upwards of 20% by weight saccharides, with at least 95 percent by weight of said saccharides being glucose. In the first step of the process, the pH and temperature of the slurry are adjusted to values suitable to promote RSH activity, and an RSH enzyme preparation of sufficient activity to promote a relatively rapid rate of starch solubilization and saccharification is added. Preferably, the reaction is allowed to proceed until at least a substantial portion, but less than all, of the starch is solubilized and the weight percent of solubilized saccharides, d.s., is at least about 22%. The resulting solution or syrup is separated, e.g., by centrifugation, filtration, etc., from the insolubles which contain the fiber, protein and fat along with a significant amount of starch that has not been solubilized in the initial step. This separation is preferably made before the glucose percentage of the solubilized saccharide drops below 95% (and most preferably before said glucose percentage drops below 97%) as it would if the first stage hydrolysis is allowed to continue overly long. The first step is generally complete within 48 hours.

In the second step, the insolubles are mixed with additional water to form a second slurry which contains less than 20% by weight, d.s., insoluble starch and preferably about 16% starch or less. Conditions of temperature and pH are adjusted to promote RSH preparation activity. Conversion of the starch is allowed to proceed in the presence of an RSH enzyme preparation until very little (e.g., generally less than about 10%, preferably less than about 5% and most preferably less than about 1%) of the starch used to form the second slurry remains unsolubilized. Any starch remaining unsolubilized following the second step hydrolysis remains with mud which is released from the starch during hydrolysis and which is comprised of fiber, protein and fat. Preferably, the syrup produced in this second step is at least 15 percent by weight saccharide, d.s. Typically, the syrups from the two steps are pooled, and if so pooled, provide a syrup which is at least about 20 weight percent saccharides, d.s. The percent of the saccharides which is glucose as a result of each of the first and second steps, individually, is preferably at least about 95 percent by weight.

The amount of starch which can be solubilized within a commercially acceptable time period in the first step before the reaction is terminated varies according to the percentage of starch in the initial slurry. For example, if the initial slurry is about 36 percent starch, only about 60 percent of the starch will generally be solubilized in the first step within a 48-hour hydrolysis period, whereas if the initial slurry is about 26 percent starch, upwards of about 85 percent of the starch is solubilized in the first step within the same hydrolysis period. The higher the starch content of the initial starch slurry, the higher the concentration of saccharide in the syrup resulting from the first step. For example, with a 36 percent starch slurry, saccharide solutions of up to about 29 percent d.s. saccharide content may be obtained in the first step without the percent glucose in the syrup dropping below 95%, whereas with a 26 percent starch slurry, saccharide solutions of about 24 percent d.s. saccharide content may be obtained without the percent glucose in the syrup dropping below 95%. In the second step, the slurry is preferably adjusted to about the highest starch percent consistent with substantially complete solubilization of the remaining starch, e.g., up to about 20 percent and preferably about 16 percent. The degree of starch solubilization and saccharide content of the syrup produced in the second step at a given second step slurry starch solids content will be substantially the same, regardless of the percent of starch used to form the initial slurry in the first step of the process. In the second step within a period of about 48 hours, in excess of 95% of the remaining starch will typically be hydrolyzed and generally in excess of 99% thereof will be hydrolyzed.

An important advantage of the invention is that the relatively high starch solids granular starch slurries which are solubilized in the first step are contained in much smaller reactor vessels than would be required if initial slurries were of a starch percentage capable of being solubilized in a single step, i.e. at less than 20 weight percent starch solids. Furthermore, much more highly concentrated syrups are produced than can be obtained from a one-step solubilization of low solids starch slurries, thereby avoiding the need for concentrating as extensively. The second step corresponds, both in initial starch concentration and in saccharide solution produced, to that of a less than 20 weight percent starch solids, one-step solubilization, but of course, at this step of the overall process, the major quantity of starch which was present in the initial starch slurry has already been solubilized and removed as syrup. In total, the entire two-step process requires substantially less reactor vessel volume and produces a pooled syrup of significantly higher concentration than can be obtained in a one-step conversion of low solids starch slurry. In a multi-step process using initial starch slurries of 20 to 60 percent, relatively little starch is lost to the fiber, protein and fat residue (i.e., "mud"), whereas in a single step process beginning with the same high starch solids level, significant quantities of starch would be lost to the mud.

Enzyme systems or preparations which are generally suitable for use in the practice of the present invention include any of those exhibiting raw starch hydrolyzing (RSH) activity or capability (i.e., RSH enzyme preparations). However, the advantages of the present invention (e.g., relative to a single step, high starch solids aqueous slurry enzyme hydrolysis process) are most pronounced in the case of those RSH enzyme preparations whose solubilization rates tend to decrease substantially in the later stages (e.g., after 50 to 60% starch solubilization) of relatively high starch solids (e.g., in excess of 20 weight percent starch contents on a total slurry weight basis), single step hydrolysis operations and/or which tend to exhibit undesirably high levels (e.g., 5 weight percent or more on a solubilized saccharide total weight basis) of di-, tri- and higher polysaccharide formation when said relatively high starch solid, single stage hydrolysis operations are carried to relatively high degrees (e.g., 95 or more) of starch conversion. Accordingly, the application or use of the present invention in conjunction with this latter type of RSH enzyme is particularly beneficial and preferred.

A particularly preferred RSH enzyme preparation for use in the present invention is the hereinbefore described Humicola RSH enzyme preparation. Said Humicola RSH enzyme preparation exhibits maximum activity within the pH range of 5.0 to 7.0 and particularly in the range of 5.5 to 6.0. Said enzyme preparation exhibits maximum activity in the temperature range of 50° C. to 65° C. In each of the steps, the enzymatic solubilization of starch is preferably carried out within these pH and temperature ranges.

Certain especially preferred Humicola RSH enzyme preparations for use in the present invention are those obtained from a fungal organism strain of *Humicola grisea* var. *thermoidea* selected from the group consisting of ATCC 16453; NRRL 15219; NRRL 15220; NRRL 15221; NRRL 15222; NRRL 15223; NRRL 15224 and NRRL 15225 (and genetically altered strains artificially derived therefrom), wherein the ATCC number represents a Deposit Type Collection Number of the American Type Culture Collection Depository in Rockville, Md. and wherein "NRRL" stands for the USDA's Northern Regional Research Laboratory in Peoria, Ill.

As noted above, Humicola RSH enzyme preparation contains glucoamylase activity as well as a potentiating factor which solubilizes raw starch. The relative proportions of potentiating factor and glucoamylase activity in other RSH enzyme preparations may vary somewhat. However, with RSH enzyme preparations of interest for use in the practice of the present invention, there is usually ample potentiating factor produced along with the glucoamylase fraction. Accordingly, for purposes of this invention, the activity of the RSH enzyme preparations is defined in terms of their glucoamylase activity.

Glucoamylase activity is measured for purposes of this invention in 10 D.E. units for either RSH enzyme preparation or conventional glucoamylase. A 10 D.E. unit is the amount of either type of enzyme which produces 1 micromole of glucose per minute under the assay conditions. To determine glucoamylase activity for purposes of this invention, one-tenth ml of enzyme preparation, diluted if necessary, containing 0.06 units to 1.1 units is added to 0.9 ml of substrate solution preheated at 50° C. for 5 minutes. The substrate solution consists of 40 parts by volume 0.25M sodium acetate buffer (pH 5.5) and 50 parts by volume 4% by weight 10 D.E. maltodextrin in water. The substrate solution is kept at 50° C. for 5 minutes before the enzyme solution is added. After 10 minutes, the reaction is quenched by pouring into a preheated 16 mm test tube and heating in a 100° C. water bath for 6 minutes. Glucose concentration is determined by any convenient method, such as glucose reagent kit No. 15-UV from Sigma Chemical Co. or with an instrument such as the Technicon Autoanalyzer.

In the first starch solubilization and saccharification step of the present invention, the RSH enzyme preparation is employed in an amount sufficient to solubilize at least a substantial portion (and preferably a major proportion) of the granular starch contained within said first starch slurry. Typically, the addition of RSH enzyme preparation to the first starch slurry in an amount corresponding to from about 2 to about 60 (preferably from about 5 to about 30) 10 D.E. units per gram of starch in said first slurry is adequate for such purpose.

In the second starch solubilization and saccharification step of the invention, the RSH enzyme preparation is employed in an amount sufficient to solubilize substantially all (e.g., in excess of 90%, preferably at least about 95%, more preferably at least about 97% and most preferably about 99% or more) of the starch contained within the second starch slurry. Here again, from about 2 to about 60 (preferably about 5 to about 30) 10 D.E. units per gram of starch in said second slurry will suffice for such purpose.

With regard to the foregoing, it should be noted that RSH enzyme preparation from the first saccharification step will oftentimes be carried over into the second starch slurry in the mud/unsolubilized starch residue from said first stage solubilization. Accordingly, the amount of RSH enzyme preparation which needs to be freshly or separately added to said second slurry to obtain the requisite second slurry enzyme content or activity may be substantially less than the numerical 10 D.E. unit ranges stated above. Indeed, in some instances, the amount of RSH enzyme preparation carried over from the first solubilization may, by itself, be totally sufficient for the second slurry solubilization step. In such instances, no separate or fresh addition of RSH enzyme preparation is required in connection with the second stage solubilization reaction.

The RSH enzyme preparation may be the unpurified broth produced, for example, by fermentation of a fungus. Alternatively, the RSH enzyme preparation may be purified to various extents to remove inactive protein. The active components of RSH enzyme preparation are not adsorbed by DEAE cellulose, e.g., Whatman pre-swollen Microgranular Anion Exchanger DE52 diethylaminoethyl cellulose, and inactive proteins are removed by adsorption to the cellulose. When exposed either to a column or bath of DEAE cellulose at a pH of 5.0 to 7.0 (preferably 6.5 to 7.0), a 2 to 4.5 fold increase in specific activity is achieved which is attributable at least in part to the removal of inactive proteins.

The relative rates of solubilization and glucose production are affected by the concentrations of calcium ion in the reaction mixture. For example, calcium at levels of about 10 to 200 ppm and preferably at levels of 30 to 100 ppm promotes RSH enzyme preparation activity and stabilizes the same with respect to slightly higher temperatures. Higher calcium levels may decrease RSH enzyme preparation activity.

Practically any starch source is suitable for the method of the present invention as RSH enzyme preparations will solubilize and saccharify all starches, both of the amylose and amylopectin varieties. However, due to practical considerations such as cost, availability, etc., corn starch represents a particularly preferred starch for use in the practice of the present invention. There is no need to specially prepare the starch, and ground whole kernel corn is a suitable corn starch source, as is degerminated yellow corn meal.

The invention will now be described in greater detail by way of the following specific examples in which all parts and percentages are on a weight basis and temperatures are in degrees Celsius unless otherwise indicated.

EXAMPLE 1

Corn starch was slurried in water at 26% d.s. starch. Calcium was added to a concentration of 30 ppm; the pH was adjusted to 5.7; and the temperature was raised to 55° C. 15 10 D.E. units of unrefined RSH enzyme preparation obtained from the fermentation broth of a mutant strain of the fungus *Humicola grisea* var. *thermoidea* (ATCC 16453) per gram of starch was added. The reaction proceeded at 55° C. for 48 hours as the slurry was stirred. About 82 percent of the initially charged starch was solubilized in this first hydrolysis step.

The slurry was filtered to separate the syrup from the insolubles and the phases were separated. The syrup was 24.0% saccharides of which 97.4% was glucose on a dry substance basis.

The insolubles were reslurried at 16% starch, d.s. and the conditions adjusted as above, including the addition of an additional 15 10 D.E. units per gm. of starch. The reaction proceeded for an additional 48 hours, after which the remaining insolubles were separated from the syrup by centrifugation. The syrup from the second reaction was 17.5% saccharides, of which 96.4%, on a dry substance basis, was glucose. The syrups were pooled producing a blended syrup product which was 22.9% saccharides, of which 97.2%, on a dry substance basis, was glucose.

The insoluble mud from centrifugation contained less than 1% of the starch initially present.

EXAMPLE 2

Corn starch was slurried in water at 36% d.s. starch. Calcium was added to a concentration of 30 ppm; the pH was adjusted to 5.7; and the temperature was raised to 55° C. 15 10 D.E. units of unrefined RSH preparation obtained from the fermentation broth of a mutant strain of the fungus *Humicola grisea* var. *thermoidea* (ATCC 16453) per gram of starch was added. The reaction proceeded at 55° C. for 48 hours as the slurry was stirred. About 64 percent of the initially charged starch material was solubilized in this first hydrolysis step.

The slurry was filtered to separate the syrup from the insolubles and the phases were separated. The syrup was 28.5% saccharides, 96.5% of which was glucose on a dry substance basis.

The insolubles were reslurried at 16% starch, d.s., and the conditions adjusted as above, including the addition of an additional 15 10 D.E. units per gm. of starch. The reacton proceeded for an additional 48 hours, after which the remaining insolubles were separated from the syrup by centrifugation. The syrup from the second reaction was 17.5% saccharides, of which 97.5% was glucose on a dry substance basis. The syrups were pooled, producing a blended syrup product which was 24.6% saccharides, of which 96.9%, on a dry substance basis, was glucose.

The insoluble mud contained less than 1% of the starch initially present.

The above examples demonstrate that excellent results are achieved through the use of enzyme with RSH activity in accordance with the present invention. In the process, substantially all of the starch is solubilized and saccharified. The combined syrups are higher than about 22% (preferably higher than about 24%) saccharide, at least about 95% (preferably at least about 96%) of which is glucose. The syrups are ideal stock for enzymatic conversion to high fructose syrup or fermentation to ethanol. Being high in saccharide content, the syrups may be concentrated or dried with less energy. When even higher initial saccharide concentrations are desired, the syrup from the first step may be used alone and the syrup from the second step used for other purposes.

The enzymatic conversion is carried out on raw starch at a relatively low temperature and avoids energy-intensive pasting. The process requires few pH adjustments and minimal additional costs.

While the invention has been described in terms of certain preferred embodiments, modifications obvious to one with ordinary skill in the art may be made without departing from the scope of the invention. For instance, while conducting the present invention in only two distinct starch slurry solubilization stages is satisfactory for most purposes and is, indeed, preferred for the sake of simplicity, those skilled in the art will, of course, recognize that the use of three or more separate and distinct starch slurry solubilization stages can also be satisfactorily employed to reap the benefits of the present invention and without departing from the spirit and scope thereof.

The present invention and various embodiments thereof are set forth in the following claims.

What is claimed is:

1. A method of preparing a syrup containing, on a dry substance weight basis, a high percentage of glucose, said method comprising:
   (a) preparing a first aqueous slurry of granular starch containing between about 20 and about 60 weight percent starch, d.s.;
   (b) adjusting the pH and the temperature of said first slurry to values suitable to promote activity of a raw starch hydrolyzing enzyme preparation which is produced by a fungal organism and which catalyzes the hydrolysis of granular starch directly to glucose, said raw starch hydrolyzing enzyme preparation being characterized in that it catalyzes the hydrolysis of granular starch suspended in water at a concentration of about 15 percent by weight starch solids substantially completely to soluble glucose syrup solids containing at least about 97 percent by weight glucose, d.s., when the hydrolysis is carried out at a pH of about 5.0 to about 7.0 and a temperature of about 55° C. and without added alpha amylase or added debranching enzyme of the pullulanase, isoamylase or beta amylase type, said enzyme preparation being further characterized in that it is separable by carboxymethyl cellulose into a first adsorbing fraction and a second non-adsorbing proteinaceous fraction, said first adsorbing fraction containing a glucoamylase enzyme (EC 3.2.1.3) that has an isoelectric point of about 8.0 or higher and said second non-adsorbing fraction having glucoamylase-protentiating activity that catalyzes the hydrolysis of granular starch;
   (c) adding to said first slurry the raw starch hydrolyzing enzyme preparation in an amount sufficient to solubilize and saccharify a substantial portion of the starch in said first slurry;
   (d) allowing said raw starch hydrolyzing enzyme preparation to solubilize and saccharify a substantial portion, but less than all, of the starch in said first slurry to yield a first syrup of at least about 22 weight percent saccharides, d.s.;
   (e) separating said first syrup from the insolubles which remain and which contain unsolubilized starch from said first slurry;
   (f) preparing a second aqueous slurry from said insolubles, said second slurry containing less than about 20 weight percent, d.s., starch;
   (g) adjusting the pH and the temperature of said second slurry to values suitable to promote raw starch hydrolyzing enzyme activity;
   (h) contacting said second slurry with the raw starch hydrolyzing enzyme preparation in an amount sufficient to solubilize and saccharify substantially all of the starch contained in said second slurry;
   (i) allowing said raw starch hydrolyzing enzyme preparation to solubilize and saccharify substantially all of the starch in said second slurry to provide a second syrup; and
   (j) separating said second syrup from insolubles contained therein.

2. A method according to claim 1 wherein the step (e) separation is made before the glucose content of the first syrup from step (d) drops below the 95 weight percent of the soluble saccharides in said first syrup.

3. A method according to claim 1 wherein step (d) is conducted over a period of about 48 hours or less.

4. A method according to claim 1 wherein said insolubles are removed from said syrups in steps (e) and (j) by centrifugation.

5. A method according to claim 1 wherein step (i) is carried out until at least about 95% of the starch in said second slurry is solubilized.

6. A method according to claim 1 wherein each of said first and second slurries contains between about 10 and about 200 ppm calcium.

7. A method according to claim 1 wherein said step (d) is conducted until at least about 25 percent of the starch in said first slurry is solubilized and saccharified.

8. The method according to claim 1 wherein said step (d) is conducted until at least about 50 percent of the starch in said first slurry is solubilized and saccharified.

9. The method according to claim 1 wherein at least about 60 percent of the starch in said first slurry is solubilized and saccharified in step (d) thereof.

10. The method according to claim 1 wherein said insolubles are removed from the syrups in steps (e) and (j) by centrifugation or filtration.

11. The method according to claim 1 wherein the first aqueous granular starch slurry contains from about 25 to about 40 weight percent granular starch on a total slurry weight basis.

12. The method according to claim 1 wherein the starch slurry of step (f) contains about 16 weight percent or less of granular starch on a total slurry weight basis.

13. The method of claim 1 wherein step (d) is terminated before the glucose content of the first syrup drops below about 97 weight percent on a soluble saccharide weight basis.

14. The method of claim 1 wherein said first and second syrups are pooled to provide a combined syrup containing in excess of 22 weight percent solubilized saccharide on a total syrup weight basis and in which at least about 95 weight percent of said saccharide is glucose.

15. The method of claim 1 wherein said first and second syrups are pooled to provide a combined syrup containing in excess of 24 weight percent solubilized saccharide on a total syrup weight basis, of which at least about 96 weight percent is glucose.

16. The method of claim 1 wherein the solubilization and saccharification of said first slurry is conducted at a pH of from about 5.0 to about 7.0 and at a temperature of from about 50° to about 65° C.

17. The method of claim 16 wherein the solubilization and saccharification of said second slurry is conducted at a pH of from about 5.0 to about 7.0 and at a temperature of from about 50° to about 65° C.

18. The method of claim 17 wherein the enzyme employed for the solubilization and saccharification of both the first and second starch slurries is a Humicola RSH enzyme.

19. The method of claim 1 wherein from about 2 to about 60 10 D.E. units of said RSH enzyme per gram of starch is employed to solubilize and saccharify each of said first and second aqueous starch slurries.

20. The method of claim 1 wherein the amount of RSH enzyme employed to solubilize and saccharify each of said first and second aqueous starch slurries is between about 5 and about 30 10 D.E. units.

21. The method of claim 1 wherein the granular starch employed is derived from corn.

22. A method of preparing a syrup containing, on a dry substance weight basis, a high percentage of glucose, said method comprising:
(a) preparing a first aqueous slurry of granular starch containing between about 20 and about 60 weight percent starch, d.s.;
(b) adjusting the pH and the temperature of said first slurry to values suitable to promote activity of a raw starch hydrolyzing enzyme preparation which is produced by a fungal organism that is a strain of the genus Humicola and which catalyzes the hydrolysis of granular starch directly to glucose, said raw starch hydrolyzing enzyme preparation being characterized in that it catalyzes the hydrolysis of granular starch suspended in water at a concentration of about 15 percent by weight starch solids substantially completely to soluble glucose syrup solids containing at least about 97 percent by weight glucose, d.s., when the hydrolysis is carried out at a pH of about 5.0 to about 7.0 and a temperature of about 55° C. and without added alpha amylase or added debranching enzyme of the pullulanase, isoamylase or beta amylase type, said enzyme preparation being further characterized in that it is separable by carboxymethyl cellulose into a first adsorbing fraction and a second non-adsorbing proteinanceous fraction, said first adsorbing fraction containing a glucoamylase enzyme (EC 3.2.1.3) that has an isoelectric point of about 8.0 or higher and said second non-adsorbing fraction having glucoamylase-protentiating activity that catalyzes the hydrolysis of granular starch;
(c) adding to said first slurry the raw starch hydrolyzing enzyme preparation in an amount sufficient to solubilize and saccharify a substantial portion of the starch in said first slurry;
(d) allowing said raw starch hydrolyzing enzyme preparation to solubilize and saccharify a substantial portion, but less than all, of the starch in said first slurry to yield a first syrup of at least about 22 weight percent saccharides, d.s.;
(e) separating said first syrup from the insolubles which remain and which contain unsolubilized starch from said first slurry;
(f) preparing a second aqueous slurry from said insolubles, said second slurry containing less than about 20 weight percent, d.s., starch;
(g) adjusting the pH and the temperature of said second slurry to values suitable to promote raw starch hydrolyzing enzyme activity;
(h) contacting said second slurry with the raw starch hydrolyzing enzyme preparation in an amount sufficient to solubilize and saccharify substantially all of the starch contained in said second slurry;
(i) allowing said raw starch hydrolyzing enzyme preparation to solubilize and saccharify substantially all of the starch in said second slurry to provide a second syrup; and
(j) separating said second syrup from insolubles contained therein.

23. A method of preparing a syrup contaning, on a dry substance weight basis, a high percentage of glucose, said method comprising:
(a) preparing a first aqueous slurry of granular starch containing between about 20 and about 60 weight percent starch, d.s.;
(b) adjusting the pH and the temperature of said first slurry to values suitable to promote activity of a raw starch hydrolyzing enzyme preparation which is produced by a fungal organism that is a strain of the species *Humicola grisea* and which catalyzes the hydrolysis of granular starch directly to glucose, said raw starch hydrolyzing enzyme preparation being characterized in that it catalyzes the hydrolysis of granular starch suspended in water at a concentration of about 15 percent by weight starch solids substantially completely to soluble glucose syrup solids containing at least about 97 percent by weight glucose, d.s., when the hydrolysis is carried out at a pH of about 5.0 to about 7.0 and a temperature of about 55° C. and without added alpha amylase or added debranching enzyme of the pullulanase, isoamylase or beta amylase type, said enzyme preparation being further characterized in that it is separable by carboxymethyl cellulose into a first adsorbing fraction and a second non-adsorbing proteinaceous fraction, said first adsorbing fraction containing a glucoamylase enzyme (EC 3.2.1.3) that has an isoelectric point of about 8.0 or higher and said second non-adsorbing fraction having glucoamylase-protentiating activity that catalyzes the hydrolysis of granular starch;
(c) adding to said first slurry the raw starch hydrolyzing enzyme preparation in an amount sufficient to solubilize and saccharify a substantial portion of the starch in said first slurry;
(d) allowing said raw starch hydrolyzing enzyme preparation to solubilize and saccharify a substantial portion, but less than all, of the starch in said first slurry to yield a first syrup of at least about 22 weight percent saccharides, d.s.;
(e) separating said first syrup from the insolubles which remain and which contain unsolubilized starch from said first slurry;
(f) preparing a second aqueous slurry from said insolubles, said second slurry containing less than about 20 weight percent, d.s., starch;

(g) adjusting the pH and the temperature of said second slurry to values suitable to promote raw starch hydrolyzing enzyme activity;

(h) contacting said second slurry with the raw starch hydrolyzing enzyme preparation in an amount sufficient to solubilize and saccharify substantially all of the starch contained in said second slurry;

(i) allowing said raw starch hydrolyzing enzyme preparation to solubilize and saccharify substantially all of the starch in said second slurry to provide a second syrup; and (j) separating said syrup from insolubles contained therein.

24. A method of preparing a syrup containing, on a dry substance weight basis, a high percentage of glucose, said method comprising:

(a) preparing a first aqueous slurry of granular starch containing between about 20 and about 60 weight percent starch, d.s.;

(b) adjusting the pH and the temperature of said first slurry to values suitable to promote activity of a raw starch hydrolyzing enzyme preparation which is produced by a fungal organism that is a strain of the species *Humicola grisea* var. *thermoidea* and which catalyzes the hydrolysis of granular starch directly to glucose, said raw starch hydrolyzing enzyme preparation being characterized in that it catalyzes the hydrolysis of granular starch suspended in water at a concentration of about 15 percent by weight starch solids substantially completely to soluble glucose syrup solids containing at least about 97 percent by weight glucose, d.s., when the hydrolysis is carried out at a pH of about 5.0 to about 7.0 and a temperature to about 55° C. and without added alpha amylase or added debranching enzyme of the pullulanase, isoamylase or beta amylase type, said enzyme preparation being further characterized in that it is separable by carboxymethyl cellulose into a first adsorbing fraction and a second non-adsorbing proteinaceous fraction, said first adsorbing fraction containing a glucoamylase enzyme (EC 3.2.1.3) that has an isoelectric point of about 8.0 or higher and said second non-adsorbing fraction having glucoamylase-protentiating activity that catalyzes the hydrolysis of granular starch;

(c) adding to said first slurry the raw starch hydrolyzing enzyme preparation in an amount sufficient to solubilize and saccharify a substantial portion of the starch in said first slurry;

(d) allowing said raw starch hydrolyzing enzyme preparation of solubilize and saccharify a substantial portion, but less than all, of the starch in said first slurry to yield a first syrup of at least about 22 weight percent saccharides, d.s.;

(e) separating said first syrup from the insolubles which remain and which contain unsolubilized starch from said first slurry;

(f) preparing a second aqueous slurry from said insolubles, said second slurry containing less than about 20 weight percent, d.s., starch;

(g) adjusting the pH and the temperature of said second slurry to values suitable to promote raw starch hydrolyzing enzyme activity;

(h) contacting said second slurry with the raw starch hydrolyzing enzyme preparation in an amount sufficient to solubilize and saccharify substantially all of the starch contained in said second slurry;

(i) allowing said raw starch hydrolyzing enzyme preparation to solubilize and saccharify substantially all of the starch in said second slurry to provide a second syrup; and (j) separating said second syrup from insolubles contained therein.

* * * * *